(12) United States Patent
Breffa et al.

(10) Patent No.: US 8,334,318 B2
(45) Date of Patent: Dec. 18, 2012

(54) ANIONIC ISOSORBIDE DERIVATIVES AND THEIR USE (II)

(75) Inventors: Catherine Breffa, Düsseldorf (DE); Hans-Christian Raths, Monheim (DE); Ansgar Behler, Bottrop (DE)

(73) Assignee: Cognis IP Management GmbH, Duesseldorf (DE)

( * ) Notice: Subject to any disclaimer, the term of this patent is extended or adjusted under 35 U.S.C. 154(b) by 197 days.

(21) Appl. No.: 12/961,070

(22) Filed: Dec. 6, 2010

(65) Prior Publication Data

US 2011/0135583 A1    Jun. 9, 2011

(30) Foreign Application Priority Data

Dec. 5, 2009  (EP) .................................... 09015093

(51) Int. Cl.
*A61K 31/34*    (2006.01)
*C07D 493/02*   (2006.01)

(52) U.S. Cl. ....................... 514/470; 549/464
(58) Field of Classification Search .................. 514/470; 549/464
See application file for complete search history.

(56) References Cited

U.S. PATENT DOCUMENTS

| | | |
|---|---|---|
| 2002/0174596 A1 | 11/2002 | Deflort et al. |
| 2004/0241099 A1 | 12/2004 | Popp et al. |

FOREIGN PATENT DOCUMENTS

| | | |
|---|---|---|
| GB | 1523644 | 9/1978 |
| WO | 01/01949 A1 | 1/2001 |

OTHER PUBLICATIONS

European Search Report dated Apr. 29, 2010 from EP Appln. No. 09015093.9.

*Primary Examiner* — Taofiq A Solola
(74) *Attorney, Agent, or Firm* — Diehl Servilla LLC

(57) ABSTRACT

Disclosed are isosorbide derivatives of formula (I)

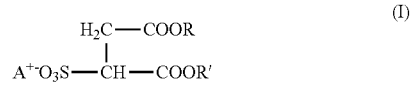

wherein R and R' independently represent an isosorbide moiety, a hydrogen atom, or an alkyl group having 6 to 22 carbon atoms, and A stands for hydrogen, an alkali metal, ammonium or alkylammonium, with the proviso that at least one of R and R' is an isosorbide group. Also disclosed is the use of compounds (I) for the preparation of cleansers, detergents, personal care compositions, and cosmetic or pharmaceutical compositions.

17 Claims, 1 Drawing Sheet

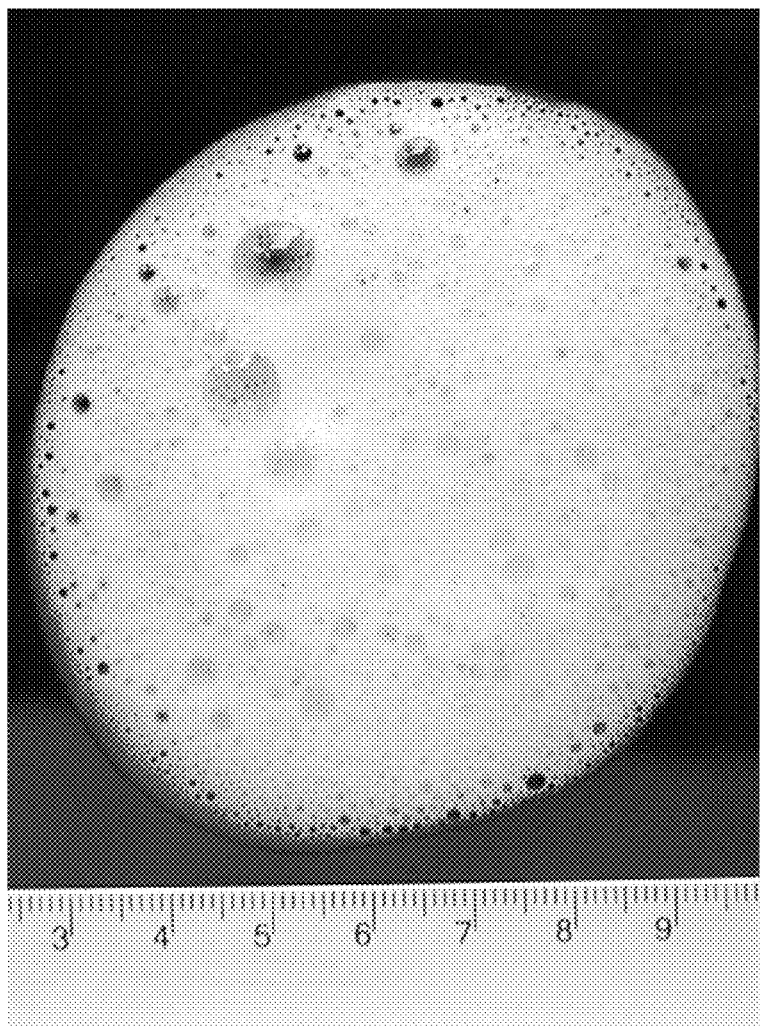
Foam quality of the product of Example 1.

ANIONIC ISOSORBIDE DERIVATIVES AND THEIR USE (II)

CROSS-REFERENCE TO RELATED APPLICATIONS

This application claims the benefit of priority under 35 USC §119 of European Patent Application number 09015093.9, filed on Dec. 5, 2009, which is incorporated by reference herein in its entirety.

FIELD OF THE INVENTION

The present application pertains to specific anionic derivatives of isosorbide, and their use in household products, such as detergents, or in cosmetic applications. Preferably, the compounds are used in personal cleaning applications, detergents and manual dishwashing detergents.

BACKGROUND OF THE INVENTION

The most widely used anionic surfactants in cleansing compositions are alkyl sulphates, polyoxyethylene alkyl sulphates and alkyl benzene sulphonates. These compounds are known to have good foaming and cleaning power. Due to their harshness, however, they are not desirable as components for cleansing compositions topically applied to human skin and hair. Their damaging effect, particularly where young, tender or damaged skin is involved, has been the subject of intense study for many years.

On the other hand milder surfactants often suffer from the disadvantage that they do not provide high foaming activity, which is very important for the consumer. Therefore, there is a long-felt need for products which are not only very mild but also possess an excellent foaming power.

Isosorbide (or 1,4:3,6-dianhydrosorbitol, see formula below) is the anhydride of sorbitol:

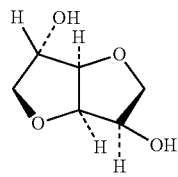

Upon heating sorbitol for example with concentrated sulfuric or hydrochloric acid, two molecules of water are eliminated with the formation of isosorbide. So far, these compounds are also known generally as dianhydrohexitols (including besides isosorbide also the isomers isomannide and isoidide).

Certain derivatives of isosorbide are known, especially esters or ethers thereof. Furthermore it is known to use certain isosorbide derivatives as additives in various applications, such as detergents, cleansers or cosmetic compositions. US 2002/0174596 A1 discloses various isosorbide ethers as detergent for fuels. WO 01/01949 A1 describes dimethylisosorbide as a component of a personal cleansing composition.

It was an object of the present invention to find new additives, useful in detergents and cleansers, based on isosorbide chemistry. It was found that certain anionic derivatives of isosorbide could be used with advantage in detergent, cleansers and related products, and most preferably in personal cleaning applications.

BRIEF DESCRIPTION OF THE DRAWINGS

FIG. 1 shows the foam quality of the product of Example 1.

DETAILED DESCRIPTION OF PREFERRED EMBODIMENTS

The present application pertains in a first embodiment to isosorbide derivatives according to general formula (I):

wherein R and R' independently from each other represent a isosorbide moiety or a hydrogen atom, or an alkyl group with 6 to 22 carbon atoms, and A stands for hydrogen, an alkali metal, ammonium or an alkylammonium, with the proviso that at least one group R or R' is an isosorbide group.

Compounds according to formula (I) are sulfosuccinate mono- or -diesters of isosorbide. Sulfosuccinates as such are well-known compounds, and a broad variety is described including their synthesis in GB 1,523,644. Synthesis of sulfosuccinates takes place, for example, by reaction of maleic anhydride in the presence of acid catalysts together with the alcohol component. Subsequently, through addition of hydrogen sulfite or sodium sulfite the transformation into the sulfosuccinate esters occurs.

The isosorbide group is represented by formula (II):

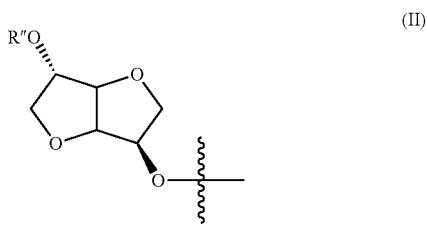

wherein one of the hydroxyl-groups of the isosorbide skeleton is linked with at least one of the carboxylic acid groups in the sulfosuccinates via an ester linkage. R" represents either a hydrogen atom, or an alkyl or alkenyl group having 1 to 22 carbon atoms.

The sulfosuccinates according to the invention may be esterified in both carboxylic acid groups with an isosorbide moiety, but preferably only one of the groups R or R' in general formula (I) represents such a group (II). It is preferred that, besides one required isosorbide ester, the compounds according to formula (I) contain either a free carboxylic acid group (R or R' stands for a hydrogen atom), or a long chain alkyl or alkenyl ester, with R or R' having 6 to 22 carbon atoms. The saturated or unsaturated C6-C22 R/R' group can be linear or branched. Preferred compounds (I) are isosorbide monoesters with the other R/R' group being hydrogen; that is, preferably the compounds (I) are mixed esters/acids.

A further preferred embodiment pertains to such derivatives according to formula (I) wherein R or R' stand for one isosorbide group according to formula (II), and the other group R or R' is a hydrogen atom, whereby in formula (II) R" preferably represents an alkyl- or alkenyl group with 1 to 22 carbon atoms, and in particular 6 to 18 carbon atoms, which could be linear or branched, saturated or unsaturated. These compounds according to formula (II) are isosorbide ether moieties.

The compounds following to formula (I) are useful for the preparation of all kinds of detergents, cleansers and the like (solid, liquid or gel-like) or the use of these compounds in cosmetic or pharmaceutical compositions. Preferred is the use of compounds according to formula (I) in cleaners, and in particular for cleaners for hard surfaces, such as kitchen or bathroom cleaners or dish washing detergents (manual and automatic). However, cosmetic compositions and personal care applications are also possible.

The isosorbide derivatives according to formula (I) may be present in amounts from about 0.1 to about 25% by weight, based on the composition, depending on the particular formulation. Preferably, detergents or cleansers will contain the isosorbide derivatives in an amount of about 1 to about 15 wt %, and most preferably about 5 to about 10 wt %, based on the total weight of the cleanser or detergent composition.

The isosorbide derivatives according to formula (I) are particularly useful in home care applications, such as detergents, and all types of cleaners (kitchen, bathroom, hard surface, automotive or car cleansers, and multipurpose cleansers), as well as in dishwashing compositions (hand and automatic dish washing) and in personal care compositions, especially in hair and body cleansing formulations, but can also used with advantage in cosmetic compositions, for example in shampoos, creams and the like.

Preferred is the use of the isosorbide derivatives, inter alia, in personal care compositions such as a liquid soap, shampoo, foam bath, shower bath and the like, or in a solid form such as a bar which can illustratively be a soap or syndet composition. The isosorbide derivatives can also be used in toothpaste and related compositions, such as mouth wash. In addition to surfactants or surfactant combinations, the cosmetic products in question typically contain such constituents as emulsifiers, oil components, solubilizers, thickeners, superfatting agents, biogenic agents, film formers, fragrances, dyes, pearlescers, foam stabilizers, preservatives and pH regulators. Accordingly, the preparations according to the invention may contain additional components and auxiliaries as known in the art.

Any detergent or cleanser compositions according to the invention may contain, besides the isosorbide derivatives other surfactants, builders, salts, bleaching agents, bleach activators, optical brighteners, redeposition inhibitors, soil repellants, solubilizers, foam inhibitors, perfumes, buffers, non-aqueous solvents, dyes and enzymes as auxiliaries and additives.

The cleaners according to the invention may further contain, for example, solubilizers, such as ethanol, isopropyl alcohol, ethylene glycol, diethylene glycol or, preferably, butyl diglycol; foam regulators, for example soap; soluble builders, for example citric acid or sodium citrate; EDTA or NTA; and abrasives as auxiliaries. In many cases, an additional bactericidal effect is required so that the multipurpose cleaners may contain cationic surfactants or biocides, for example glucoprotamine. The cleaners according to the invention may be both alkaline (pH >7.5) and acidic (pH <6.5). The isosorbide derivatives may be formulated with other surfactants, including anionic, nonionic, amphoteric and/or cationic surfactants.

Anionic surfactants according to the present invention include aliphatic sulfates, such as fatty alcohol sulfates, fatty alcohol ether sulfates, fatty acid polyglycol ester sulfates, dialkyl ether sulfates, monoglyceride sulfates and aliphatic sulfonates, such as alkane sulfonates, olefin sulfonates, ether sulfonates, n-alkyl ether sulfonates, ester sulfonates, and lignin sulfonates. Fatty acid cyanamides, sulfosuccinic acid esters, fatty acid isethionates, acylaminoalkane sulfonates (fatty acid taurides), fatty acid sarcosinates, ether carboxylic acids and alkyl (ether) phosphates may also be used for the purposes of the invention, but are not preferred. Preferred anionic surfactants in the sense of the present invention are selected from the group consisting of fatty alcohol sulfates, fatty alcohol ether sulfates, fatty acid polyglycol ester sulfates, and mixtures thereof.

Typical examples of nonionic surfactants are alkoxylates of alkanols, end-capped alkoxylates of alkanols with no free OH groups, alkoxylated fatty acid lower alkyl esters, amine oxides, alkylphenol polyglycol ethers, fatty acid polyglycol esters, fatty acid amide polyglycol ethers, fatty amine polyglycol ethers, alkoxylated triglycerides, mixed ethers and mixed formals, fatty acid-N-alkyl glucamides, protein hydrolyzates (more to particularly wheat-based vegetable products), polyol fatty acid esters, sugar esters, sorbitan esters and polysorbates. If the nonionic surfactants contain polyglycol ether chains, they may have a conventional homolog distribution although they preferably have a narrow homolog distribution. The other nonionic surfactants are preferably selected from the group consisting of alkoxylates of alkanols, more particularly fatty alcohol polyethylene glycol/polypropylene glycol ethers or fatty alcohol polypropylene glycol/polyethylene glycol ethers, end-capped alkoxylates of alkanols, more particularly end-capped fatty alcohol polyethylene glycol/polypropylene glycol ethers or end-capped fatty alcohol polypropylene glycol/polyethylene glycol ethers, and fatty acid lower alkyl esters and amine oxides.

Alkyl and alkenyl oligoglycosides are known, and preferred, nonionic surfactants which correspond to formula R—O—$[G]_p$ in which R is an alkyl and/or alkenyl group containing 6 to 22 carbon atoms, G is a sugar unit containing 5 or 6 carbon atoms and p is a number of 1 to 10. They may be obtained by the relevant methods of preparative organic chemistry. The alkyl and/or alkenyl oligoglycosides may be derived from aldoses or ketoses containing 5 or 6 carbon atoms, preferably glucose. Accordingly, the preferred alkyl and/or alkenyl oligoglycosides are alkyl and/or alkenyl oligoglucosides. The index p indicates the degree of oligomerization (DP), i.e. the distribution of mono- and oligoglycosides, and is a number of 1 to 10. Whereas p in a given compound must always be an integer and, above all, may assume a value of 1 to 6, the value p for a certain alkyl oligoglycoside is an analytically determined calculated quantity which is generally a fractional number. Alkyl and/or alkenyl oligoglycosides having an average degree of oligomerization p of 1.1 to 3.0 are preferably used. Alkyl and/or alkenyl oligoglycosides having a degree of oligomerization of less than 1.7 and, more particularly, between 1.2 and 1.4 are preferred from the application point of view. The alkyl or alkenyl group R may be derived from primary alcohols containing 4 to 11 and preferably 8 to 10 carbon atoms.

Typical examples of cationic surfactants are quaternary ammonium compounds and quaternized fatty acid trialkanolamine esters. Typical examples of amphoteric or zwitterionic surfactants are alkyl betaines, alkyl amidobetaines, aminopropionates, aminoglycinates, imidazolinium betaines and sulfobetaines.

A further preferred embodiment of the present invention pertains to the use of the isosorbide derivatives according to formula (I) in the presence of electrolyte salts as thickening agent for aqueous systems, and especially for those surfactant mixes, which are difficult to thicken. In this regard "thickening" simply means any increase of viscosity of the aqueous compositions. The isosorbide derivatives will act in combination with an electrolyte salt, such as sodium, potassium or magnesium salts, ammonium salts or inorganic sulfates. Suitable inorganic electrolyte salts are any water-soluble alkali metal, ammonium or alkaline earth metal salts, for example the fluorides, chlorides, bromides, sulfates, phosphates and nitrates and hydrogen carbonates, providing they are soluble in water in a quantity of at least 1% by weight at 20° C. The chlorides or sulfates of alkali metals, ammonium or magnesium are preferably used, with sodium chloride and magnesium chloride being particularly preferred.

The sulfosuccinates according to the invention show good detergency, and in addition also provide superior foaming properties, when compared with other known surfactants such as alkoxylated ether sulfates. Foaming properties of interest include foam volume and tactile properties of the foam. The latter is specifically important and advantageous in the formulation of hand detergents, manual dishwashing detergents, and personal care as well as cosmetic compositions. Preferred applications for the isosorbide derivatives of the invention are as adjuvants or surfactants in shampoos, shower gels and the like.

A further embodiment of the invention is a liquid, gel-like or solid cleaner composition, comprising at least 0.1% by weight, preferably about 0.1 to about 25% by weight, based on the composition, of one or more isosorbide derivatives of formula (I), as a surfactant component.

Other embodiments of the invention include, without limitation:

A method of preparing a cleaning composition, comprising the step of adding one or more isosorbide derivatives of claim 1 to a cleaning composition base. The isosorbide derivatives can be added in amounts from about 0.1 to about 25% by weight, preferably about 5 to about 10% by weight, based on the composition.

A method of preparing a detergent composition, comprising the step of adding one or more isosorbide derivatives of claim 1 to a detergent composition base. The isosorbide derivatives can be added in amounts from about 0.1 to about 25% by weight, preferably about 5 to about 10% by weight, based on the composition.

A method of preparing a personal care composition, comprising the step of adding one or more isosorbide derivatives of claim 1 to a personal care composition base. The isosorbide derivatives can be added in amounts from about 0.1 to about 25% by weight, based on the composition.

A method of preparing a cosmetic composition, comprising the step of adding one or more isosorbide derivatives of claim 1 to a cosmetic composition base. The isosorbide derivatives can be added in amounts from about 0.1 to about 25% by weight, based on the composition.

A method of preparing a pharmaceutical composition, comprising the step of adding one or more isosorbide derivatives of claim 1 to a pharmaceutical composition base. The isosorbide derivatives can be added in amounts from about 0.1 to about 25% by weight, based on the composition.

The following examples are intended to be illustrative of the present invention, and in no way limit its scope.

EXAMPLES

Preparation of an Isosorbide Sulfosuccinate

Example 1

Synthesis of Isosorbide Lauroylester Sulfosuccinate

Isosorbide mono-lauroylester (1 mol) and sodium carbonate (0.05 mol) are heated to 65-70° C. under inert atmosphere. Maleic anhydride is added portionwise and the mixture is heated to 80° C. for 2 h. The hot reaction mixture is then poured into a cold sodium sulfite aqueous solution (1 mol, 0.4 mol/L) and the resulting mixture is stirred for 2 more hours at 75° C. under an inert atmosphere. 500 mL water is added to yield a white viscous liquid containing 30% of isosorbide lauroylester sulfosuccinate as active substance.

Performance Tests of the Isosorbide Sulfosuccinates

The foam quality and foam volume of this surfactant was tested as follows:

The isosorbide sulfosuccinate is dissolved in water at a rate of 2.5% active substance, and stirred to foam under standard conditions. According to a visual evaluation the surfactant of Example 1 has a foam quality of 4-5 on a scale of 1 (small bubbles, high cushion, stable foam) to 5 (large bubbles, unstable foam), and a foam volume equal to 32% of the foam for a standard surfactant (see FIG. 1).

What is claimed is:
1. An isosorbide derivative of formula (I):

$$H_2C-COOR$$
$$A^+{}^-O_3S-CH-COOR' \quad (I)$$

wherein R and R' independently represent an isosorbide moiety, a hydrogen atom, or an alkyl group having 6 to 22 carbon atoms, and A stands for hydrogen, an alkali metal, ammonium or alkylammonium,
with the proviso that at least one of R and R' is an isosorbide group.

2. The isosorbide derivative of claim 1, wherein only one of R and R' represents an isosorbide group of formula (II):

(II)

wherein R" stands for a hydrogen atom, or an alkyl- or alkenyl group having 1 to 22 carbon atoms.

3. A liquid, gel-like or solid cleaner composition, comprising at least 0.1% by weight, based on the composition, of one or more isosorbide derivatives of claim 1 as a surfactant.

4. A liquid, gel-like or solid cleaner composition, comprising about 0.1 to about 25% by weight, based on the composition, of one or more isosorbide derivatives of claim 1 as a surfactant.

5. The liquid, gel-like or solid cleaner composition of claim 4, comprising about 5 to about 10% by weight, based on the composition, of one or more isosorbide derivatives of claim 1.

6. A method of preparing a cleaning composition, comprising the step of adding one or more isosorbide derivatives of claim 1 to a cleaning composition base.

7. A method of preparing a detergent composition, comprising the step of adding one or more isosorbide derivatives of claim 1 to a detergent composition base.

8. A method of preparing a personal care composition, comprising the step of adding one or more isosorbide derivatives of claim 1 to a personal care composition base.

9. A method of preparing a cosmetic composition, comprising the step of adding one or more isosorbide derivatives of claim 1 to a cosmetic composition base.

10. A method of preparing a pharmaceutical composition, comprising the step of adding one or more isosorbide derivatives of claim 1 to a pharmaceutical composition base.

11. The method of claim 6, wherein said isosorbide derivative is added in amounts from about 0.1 to about 25% by weight, based on the composition.

12. The method of claim 7, wherein said isosorbide derivative is added in amounts from about 0.1 to about 25% by weight, based on the composition.

13. The method of claim 8, wherein said isosorbide derivative is added in amounts from about 0.1 to about 25% by weight, based on the composition.

14. The method of claim 9, wherein said isosorbide derivative is added in amounts from about 0.1 to about 25% by weight, based on the composition.

15. The method of claim 10, wherein said isosorbide derivative is added in amounts from about 0.1 to about 25% by weight, based on the composition.

16. The method of claim 6, wherein said isosorbide derivative is added in amounts from about 5 to about 10% by weight, based on the composition.

17. The method of claim 7, wherein said isosorbide derivative is added in amounts from about 5 to about 10% by weight, based on the composition.

* * * * *